United States Patent [19]
Haas

[11] Patent Number: 6,141,572
[45] Date of Patent: Oct. 31, 2000

[54] PROCESS AND SYSTEM FOR SIMULTANEOUSLY SIMULATING ARTERIAL AND NON-ARTERIAL BLOOD OXYGEN VALUES FOR PULSE OXIMETRY

[75] Inventor: Peter Haas, East Fairfield, Vt.

[73] Assignees: Bio-Tek Instruments, Inc., Winooski, Vt.; Lionheart Technologies, Inc., Carson City, Nev.; BTI Holdings, Inc., Winooski, Vt.

[21] Appl. No.: 09/252,013

[22] Filed: Feb. 18, 1999

[51] Int. Cl.[7] .................................................... A61B 5/00
[52] U.S. Cl. ........................................ 600/331; 250/252.1
[58] Field of Search .................................. 600/310, 322, 600/323, 331, 336; 250/252.1

[56] References Cited

U.S. PATENT DOCUMENTS

Re. 36,620  3/2000  Costello, Jr. ......................... 250/252.1
5,348,005  9/1994  Merrick et al. .

Primary Examiner—Eric F. Winakur
Attorney, Agent, or Firm—Sughrue, Mion, Zinn, Macpeak & Seas, PLLC

[57] ABSTRACT

A problem in pulse oximetry is discriminating between arterial and non-arterial oxygen. Non-arterial oxygen can become detectable by an oximeter when a patient moves, obscuring the oximeter's measurement of arterial oxygen at critical times. Recent advances in pulse oximetry have made it possible to make the discrimination between arterial and non-arterial blood oxygen values. To allow manufacturers, hospitals, and medical researchers to evaluate the new oximetry technology, and evaluate oximeters which use it, new simulation technology is presented which can simulate simultaneous arterial and non-arterial blood oxygen on demand, with precision as to oxygen value, waveform amplitude, and waveform frequency. This invention provides the required simulation by double amplitude modulating the red and infra-red oximeter pulses.

43 Claims, 4 Drawing Sheets

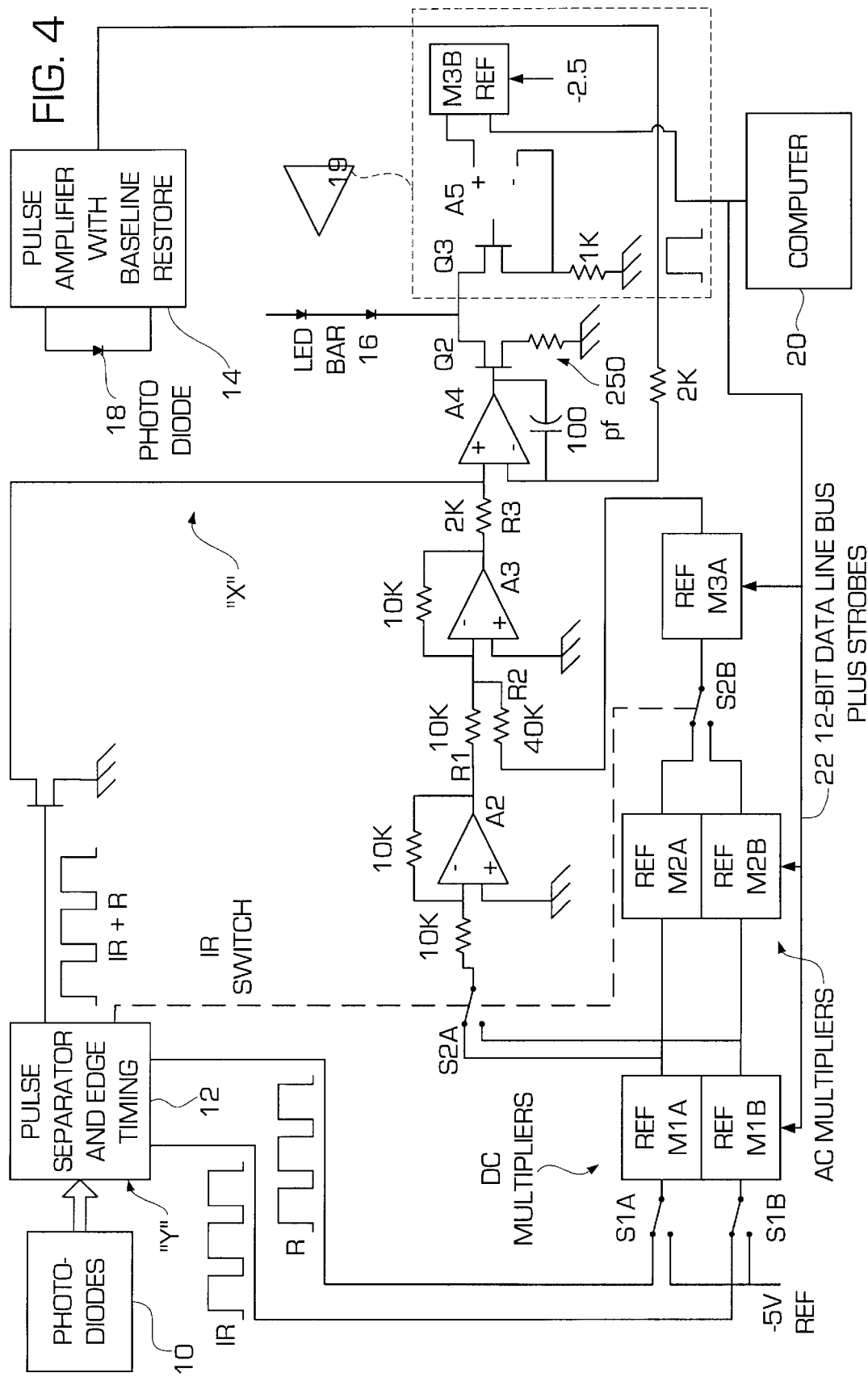

PROCESS AND SYSTEM FOR SIMULTANEOUSLY SIMULATING ARTERIAL AND NON-ARTERIAL BLOOD OXYGEN VALUES FOR PULSE OXIMETRY

BACKGROUND OF THE INVENTION

1. Field of the Invention

This invention relates to the simulation of living tissue monitored by a pulse oximeter. In particular it relates to simulation of arterial and non-arterial blood oxygen characteristics as may be measured by a pulse oximeter.

2. Description of the Related Art

Pulse oximeters to date have been designed to detect the oxygenation of arterial blood by using the differential absorption of hemoglobin by red and infra-red light as a mechanism for determining blood oxygen. Specifically, the oximeter alternately illuminates tissue (for example, here, one side of a finger) with alternating flashes of red and infra-red light of constant amplitude and at a repetition rate that is high compared to the maximum heartbeat rate. As the heart takes a beat the finger expands and contracts slightly, increasing the path length, and thereby the attenuation of the light applied to the finger. The attenuated light is captured by a photodetector, and the now amplitude modulated light flashes are processed to determine blood oxygen by detecting the red and infra-red heartbeat created modulation waves and processing them.

Simulators, used to evaluate oximeter performance, have therefore essentially been attenuators and amplitude modulators, taking the red and infra-red light flashes and/or their electrical analogues, and attenuating and amplitude modulating them as would living tissue.

There is, however, a problem with the practical use of oximetry as described above. If the patient moves then the motion could also change the path length through the monitored tissue, creating a modulation based not on arterial pressure related to expansion/contraction alone but also on expansion/contraction of tissue containing non-arterial blood. The oxygenation level of non-arterial blood tissues is at a lower value than that of the arterial blood tissues. Also, the amplitude of modulation caused by motion can be much higher than the arterial value. The result is that the oximeter can lock onto the motion signal and misread the blood oxygen value. This is a serious problem when, for example, a patient leaves the operating room and oximetry is disturbed by shivering. In other words, the oximeter may fail just as its information is needed most.

However, new oximeters have arrived on the market which appear to be able to discriminate between arterial and non-arterial blood oxygenation. These will require a new type of simulator for testing; one which can simultaneously simulate arterial and non-arterial blood characteristics; pulse shape, amplitude, and oxygenation level.

These new oximeters take advantage of the fact that in an unmoving hand (or other body part upon which oximetry is practiced), the pulsatile spectrum of non-arterial blood is virtually DC, but in a motion situation, a non-arterial "pulse" is created by virtue of the motion of the body compressing and decompressing the non-arterial tissues and changing the optical path length from oximeter probe emitter to sensor. The result of motion therefore is a non-arterial "pulse" in addition to the cardiac generated arterial pulse. The above definition of "non-arterial pulse" is used throughout the specification. The two pulses (arterial and non-arterial) naturally have differing frequency spectra. The differing spectra provide an opportunity for:

a. Separation of the two pulses using modern signal processing techniques, despite the fact that their detection is simultaneous by the oximeter;

b. Using the red/infra-red ratio of each of the separated pulses to obtain an oxygenation value for each; and c. Choosing the higher oxygen value as the arterial.

Current oximetry simulator design is shown in FIG. 1. An oximeter 1 consists in part of an LED driver 2 which normally drives current to illuminate either a red or infra-red LED. The simulator 3 captures these drive currents with a current sensor 4 which creates analogs of the drive currents at point "Y".

The current sensor may be any of the current sensors in the related art, including at least:

a. The use of current sensing resistors;

b. The use of current transformers;

c. The use of opto couplers.

Of these, the use of opto couplers may provide a more realistic simulation, as the LED driver is actually driving LEDs. In fact, the oximeter probe LEDs may be beneficially used as one half of such an opto coupler, permitting a full oximetry simulation including the probe. Many other current sensing schemes are known in the related art and will not be further reviewed here. Included in the sensing process is some means or method for distinguishing between the analogs of the red and infra-red oximeter drive pulses; the particular means or method being one appropriate to the LED drive current sensor(s) employed. Selection of such means or methods are well within the capabilities of a skilled practitioner, and will not be discussed further here.

The captured LED current drive analogs at point "Y" are applied to modulator 5. The pulses are modulated with the red and infra-red plethysmographic wave forms in the appropriate ratios so that the pulse amplitude modulated forms of the pulses at point "X" simulate the pulse amplitude modulation that would normally be made by the pulsing of arterial blood.

In addition to being modulated, the pulses at "X" are typically attenuated. The pulses at "X" are attenuated to simulate the bulk attenuation of non-pulsatile tissue, in addition to the modulation which simulates the variable attenuation of arterial pulsatile tissue.

The attenuated, modulated pulses at point "X" are then applied to a current driver 6 which applies the modulated pulses in the form of input current to the oximeter's photo diode amplifier 7.

The current driver may be any of the current drivers well known in the related art, including:

a. Directly applying the modulated pulses across an impedance to create a current according to I=E/Z;

b. Driving a current through a transformer;

c. Driving current through an opto coupler.

Of these, the opto coupler may provide a more realistic simulation, as the current driver is actually driving an isolated photo diode, which is what the oximeter expects as its current source. In fact, the oximeter probe photo diode may be beneficially used as one half of such an opto coupler, permitting a full oximetry simulation including the probe. Many other current driving schemes are known in the related art and will not be further reviewed here.

FIG. 2 shows an expanded picture of the attenuation/modulation process. The process has three inputs:

1. The red and infra-red LED drive analogs. These are obtained from the oximeter.

2. Red and infra-red attenuation factors. These are determined within the simulator. They establish the simulated bulk attenuation of tissue.

3. Red and infra-red arterial plethysmographic modulation waveforms. These are determined within the simulator. The ratios and absolute amplitudes of these waveforms determine oxygen value and signal strength, and their fundamental frequency determines simulated heartbeats/minute.

The preceding are combined by the arterial attenuation/modulation process so that the output of the process, regardless of means or method, is related to the input by:

1. Preserving the start/stop timing of the LED drive inputs in the output pulse timing.
2. Outputting red and infra-red pulses whose unmodulated amplitude is set by the red and infra-red attenuation factors. This sets the so-called "DC" values of the pulses, as shown in FIG. 2.
3. Outputting red and infra-red pulses which are amplitude modulated by the red and infra-red plethysmographic waves, respectively, or other simulation waves, as desired. This sets the so-called "AC" values of the pulses, as shown in FIG. 2.

SUMMARY OF THE INVENTION

A more complete simulation is required for the new oximeters. It follows from the above that a realistic oximetry simulation must now also be able to:

a. Create superimposed arterial and non-arterial waveforms;

b. Give each of those waveforms an independent simulated oxygenation value;

c. Give each of those waveforms an independently set amplitude; and d. Give each of those waveforms an independently set fundamental frequency and/or waveshape.

In order to meet the above new requirements for simultaneous arterial and non-arterial tissue simulation the present invention modulates the electrical analogues at point "Y", as in FIG. 1, as both the arterial pulse and the non-arterial pulse would do. This modulation may be accomplished in a number of ways, such as:

a. Entirely mathematically by computer—that is, the dual modulation may be done in conjunction with the computer reading (by a/d conversion) the "Y" input, and the double modulated result presented directly at point "X" (by d/a conversion);

b. By computer controlled hardware in various configurations—that is, the dual modulation can also be accomplished with the mathematical operations appropriate to modulation being partly done in the computer and partly in the hardware.

An essential point of the present invention is to apply multiple modulation sources to the modulation process, where:

a. For the non-arterial modulation and the arterial modulation the red and infra-red amplitude modulation ratio percents may be chosen to represent any particular desired value of blood oxygen for each of the non-arterial and arterial waves;

b. The wave shape of the non-arterial modulation and the arterial modulation may be separately specified;

c. The fundamental frequency of the non-arterial modulation and the arterial modulation may be separately set;

d. The amplitude of the non-arterial modulation and the arterial modulation waves may be separately set; and e. The modulations are applied as appropriate to each of the current sensed electrical analogues; red and infra-red.

Thus, this invention provides the required simulation, for the new oximeters, by double amplitude modulating the red and infra-red oximeter pulses.

A general process model of the present invention is shown in FIG. 3. The general process model shown in FIG. 3 is similar to that of FIG. 2, but with the addition of a new signal source—red and infra-red motion modulation waveforms.

The red and infra-red motion modulation waveforms are determined within the simulator. The ratios and absolute amplitudes of these waveforms determine oxygen value and signal strength of the motion, and their fundamental frequency determines simulated motion waves/minute. These waves can be continuous waves as in shivering, a single wave as from a bumped probe event, or anything in between. The new signal source is combined with the others and affects the "AC" portion of the output pulses, as shown in dashed lines of FIG. 3, for both red and infra-red, as appropriate. By varying the percent ratio of the red to infra-red any desired oxygen value can be simulated. That is the present invention can test a pulse oximeter at more than just one blood oxygen level. In fact, with the present invention, a pulse oximeter can be tested at any desired blood oxygen value over the range of from 0 to 100% blood oxygen.

It should be noted that while the arterial modulation of the red or infra-red "DC" amplitude is always in the direction of further attenuation, the motion modulation may be either attenuating, augmenting, or both, depending on the source and nature of the simulated motion induced distortion of non-arterial tissue.

With this new, simultaneous, motion and plethysmographic AC modulation of the pulses output from the process it is now possible to physiologically simulate actual patient motion during arterial oximetry.

In addition to simulating actual patient motion, or a bumped probe event, it is also possible to simulate respiration effects on blood oxygenation. That is, as a patient breathes, oxygen is cyclically pulled into the lungs and transferred to the blood. The technology of the present invention can be used to simulate this cyclical oxygenation of blood due to respiration. The simulation of blood oxygenation due to respiration can be done simultaneously with the simulation of arterial oxygenation. Alternatively, the simulation of blood oxygenation due to respiration can be done simultaneously with both the arterial and non-arterial oxygenation.

BRIEF DESCRIPTION OF THE DRAWINGS

The above and other objects and advantages of the present invention will become more apparent by describing in detail a preferred embodiment thereof with reference to the accompanying drawings in which:

FIG. 4 is a circuit diagram of an oximetry simulator of the present invention.

DESCRIPTION OF THE PREFERRED EMBODIMENT

Figure 1:
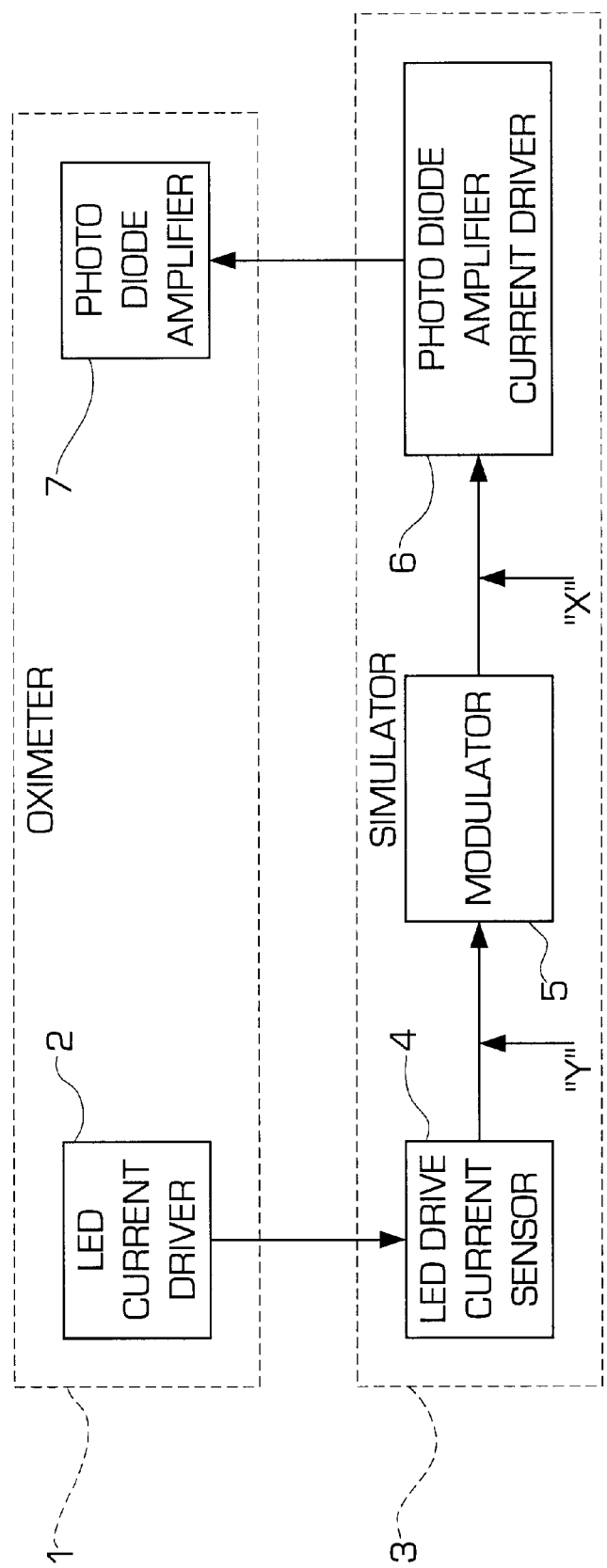
FIG. 1 is a block diagram of the related art oximetry simulator design.

A preferred embodiment of the invention will now be described with reference to FIG. 4. FIG. 4 is similar to FIG.

7 of U.S. Pat. No. 5,348,005, which patent is hereby incorporated herein by reference.

FIG. 4 is a circuit diagram of the oximeter test instrument according to an embodiment of the invention. As shown in FIG. 4, the circuitry includes a pair of photo diodes represented by the reference numeral 10 which feed a pulse separator and edge timing circuit 12, a pair of DC multipliers M1A, M1B which are coupled to the pulse separator and edge timing circuit 12 via a pair of switches S1A and S1B, respectively, a pair of AC multipliers M2A and M2B which are connected to receive the outputs of DC multipliers M1A and M1B, respectively, a multiplier M3A which is coupled to receive one of the outputs of AC multipliers M2A and M2B depending on the position of switch S2B, and a switch S2A which is coupled to selectively pass one of the outputs of DC multipliers M1A and M1B. As shown in FIG. 4, switches S1A and S1B are user controlled, whereas switches S2A and S2B are controlled according to an output of pulse separator and edge timing circuit 12. As will be discussed in greater detail below, switches S2A and S2B are controlled in accordance with detected IR flashes.

The circuitry shown in FIG. 4 further includes an amplifier A2 having an inverting terminal (−) which receives the signal passed by switch S2A, an amplifier A3 having an inverting terminal coupled to receive the output of amplifier A2 summed with the output of multiplier M3A, a servo amplifier A4 having a non-inverting terminal (+) coupled to receive the output of amplifier A3 and coupled to the drain of FET Q1 which has its source connected to ground and its gate coupled to receive an output of pulse separator and edge timing circuit 12, and an inverting terminal of amplifier A4 is coupled to receive an output of a pulse amplifier with baseline restore circuit 14. The circuit 14 is coupled to a photo diode 18 which detects light emitted from LED bar 16. In addition, the circuit of FIG. 4 includes a driving transistor Q2, an LED bar 16, an ambient light simulation circuit 19 and a computer 20 for controlling the DC multipliers M1A, M1B, the AC multipliers M2A, M2B multiplier M3A and the ambient light simulation circuit 19 via a 12-bit data line bus 22. The ambient light simulation circuit 19 includes a multiplier M3B which attenuates a DC reference signal under control of computer 20, an amplifier A5 having its non-inverting terminal (+) connected to receive an output of multiplier M3B, and a driving transistor Q3 coupled between the LED bar 16 and the output of amplifier A5.

FIG. 4 is an implementation where the coupling to the oximeter is optical, using the oximeter's probe LEDs as a cooperating half of the LED current drive current detector, and using the oximeter's probe photo diode as the cooperating half of a current driver opto isolator driving into the oximeter's photo diode amplifier input. Point "Y" of FIG. 1 is thereby similar to pulse separator 12, and point "X" of FIG. 1 is similar to the input to amplifier A4, as shown in FIG. 4.

It will be understood from the following that this invention applies to the modulation of the captured LED drive waveforms, the exact means of their capture is not of importance, and may be any of those described above or known to the art. Likewise, the current driver output configuration choice is not of consequence, and may be any of the ones described above or known to the art.

The operation of the circuitry shown in FIG. 4 will now be described.

In general, the circuitry of FIG. 4 uses one photodetector to capture the red and infra-red pulses from the pulse oximeter, and another photodetector which is filtered such that it captures infra-red pulses only.

The pulse separator and edge timing circuit 12 receives the outputs of the photo diodes 10, and in response thereto outputs four signals. A first signal IR Switch (represented by dotted lines) is a switch control signal for IR. This signal controls switches S2A and S2B, and is used to select the AC and DC corresponding to the infra-red transmission pulse wave. That is, when the pulse separator and edge timing signal receives an IR, this signal is supplied to switches S2A and S2B to select the AC and DC corresponding to the infra-red transmission pulse wave. At all other times, the red values are selected so switches S2A and S2B are in the positions shown in FIG. 4. A second signal output by circuit 12 is the red plus infra-red (R+IR) pulses. As shown in FIG. 4, this signal is supplied to the gate of FET Q1. A third signal provided by circuit 12 is an electrical analog to the pulse oximeter red flash; this signal is provided to multiplier M1A via switch S1A. The fourth signal provided by circuit 12 is an electrical analog to the pulse oximeter infra-red flash; this signal is supplied to multiplier M1B via switch S1B.

The circuit shown in FIG. 4 includes three multiplier chips M1A and M1B, M2A and M2B, and M3A and M3B. Each of these chips contains dual multiplying digital-to-analog converters (DACs) with internal output amplifiers. This eliminates the amplifiers and their associated components from the circuit board, and brings them within desired multiplier accuracy specifications.

The multipliers multiply by a computer-set value between 0 and −1; that is, the multipliers are both attenuating and inverting. Dual 12-bit multipliers are used for setting the finger density (DC attenuation) and creating the blood pressure wave form (AC attenuation); multipliers M1A, M1B and M2A, M2B, respectively. A single dual 8 bit multiplier is used to attenuate the AC wave (multiplier M3A) and control simulated ambient light (multiplier M3B). The switches S1A, S1B allow selection between the analogues of the pulse oximeter flashes (i.e., IR or R) and a fixed voltage (e.g., −5 V) as the DC references. When receiving the pulse oximeter light analogues, switches S1A, S1B are in the position shown in FIG. 4, and the multipliers M1A and M1B receive the R and IR analogues, respectively.

The attenuated DC reference voltage (i.e., the output of multipliers M1A and M1B) becomes the reference for multipliers M2A and M2B. Further, the attenuated DC reference voltage is inverted by amplifier A2. The multipliers M2A and M2B serve to create the R and IR arterial waveforms. The IR waveform has a peak multiplier setting of 1000, and the R waveform has a peak multiplier setting which varies from 400 to 3500. Multiplier M3A receives the output of either AC multiplier, depending on the position of switch S2B, and attenuates the output passing through switch S2B from its maximum value down to zero. This attenuation simulates the strength of the blood pressure wave. For example, the value zero would correspond to no heart beat. This attenuation is also for the pulse oximeter pulse loss detection test, and should allow demonstration of the pulse oximeter output in response to variance from the highest to the lowest AC/DC ratio.

Amplifier A2, inverts the positive DC levels out of multiplier M1. The inverted DC, which is now negative, is then summed with the positive AC from multiplier M3A. The DC is a negative voltage which will be proportional to base brightness, and the AC is a positive voltage representing attenuation of the blood pressure wave. The R1/R2 resistor ratio at the input of amplifier A3 sets the maximum AC at 25% of the DC applied to this summing and inverting stage. The actual AC is always less than this maximum, as the largest AC signal is only 3500/4096 times the DC out of multiplier M1A. The inverted and summed AC and DC from amplifier A3 are applied to amplifier A4 through resistor R3 and are chopped by Q1. Q1 is switched by the pulse oximeter R+IR light pulse; during the pulse, Q1 is off and amplifier A4 is driven by amplifier A3. On the other hand, when Q1 is on, the LED current (brightness) is commanded to be zero. Amplifier A4 sets the brightness for the LED bar 16 to be proportional to the input voltage of amplifier A4 when Q1 is turned off. The LED bar 16 is coupled to photo diode 18 which detects the light generated and feeds it back to amplifier A4. This is done to ensure that the LED bar output is linear. The test instrument controls the light output directly, rather than depending on the linearity and temperature stability of the LED versus the LED current.

The ambient light simulation circuit 19 includes a multiplier M3B, an amplifier A5 and a driving transistor Q3 and serves to generate a fixed current to the LED bar in addition to the red and infra-red pulses in order to simulate ambient light.

As shown in FIG. 4, the multipliers M1A, M1B, M2A, M2B, M3A and M3B are controlled by computer 20. This can be done using a simple program for setting the fixed parameters and then manipulating the R/IR ratio. The various control parameters for the multipliers are described below.

In order to provide the DC, or non-arterial, level, the circuit includes the multipliers M1A and M1B which cover the range from opaque to transparent, and is settable by the computer 20 over this range in 4,096 steps. Also, computer 20 is able to set the red and infra-red DC attenuation (i.e., multipliers M1A and M1B) separately.

As described above, multiplying DACs M1A and M1B are used as fixed attenuators of the red and infra-red light flash analogues. However, in the present invention, multiplying DACs M1A and M1B are conveniently manipulated by computer 20 to modulate in addition to attenuate. This provides the non-arterial wave modulation. The modulation percent ratios for R/IR set the oxygen level of the non-arterial pulse, and the non-arterial pulse amplitude and waveshape are under control of computer 20, similar to the arterial waves. Thus, by changing the percent ratio for R/IR, any desired oxygen level can be simulated for the non-arterial pulse. Further, by varying the percent ratio for R/IR, the present invention is able to simulate a range of oxygen values whereby a pulse oximeter can be tested at various oxygen values in that range, instead of at just one set oxygen value. In a similar manner, various oxygen values can be simulated for the arterial wave.

The (now motion modulated) outputs of M1A and M1B are fed respectively to multiplying DACs M2A and M2B where they are further modulated to simulate the arterial red and infra-red waveforms.

In order to provide the AC, or arterial, level, the circuit includes the multipliers M2A and M2B. As indicated above, these multipliers create the arterial R and IR waveforms, with the IR waveform having a peak multiplier setting of 1000, and the R waveform having a peak multiplier setting which varies from 400 to 3500.

Because of the original intent of the design, the relative amplitudes of each wave's modulation will be affected by the fact that the M1 DACs are summed with the output of the M2 DACs at amplifier A3. Obtaining an expected output means that the software wave amplitudes applied to the M1 DACs must be scaled accordingly.

The arterial AC to DC ratio corresponds to the strength of the blood pressure wave, and this ratio is simulated by multiplier M3A. One of the tasks of a pulse oximeter is to sound an alarm if the blood pressure wave is lost. Therefore, an important question is: "At what level of wave weakness is the alarm tripped?" The computer 20 is able to set the wave amplitude (i.e., multiplier M3A) from zero up to approximately 20% of the DC level in 256 steps.

A blood pressure wave corresponding to one heartbeat is generated by the computer 20 feeding the AC multipliers M2A, M2B a series of 64 numbers corresponding to blood pressure amplitude, starting at zero and returning to zero. The series of 64 numbers then repeats to form the next beat. The 64 numbers are selected such that if the series of numbers were plotted against time, then the resulting curve would be a blood pressure wave corresponding to one heart beat. A simulated heart rate is established by the computer 20 setting the time between the presentation of each of the 64 numbers. For example, if they are presented to the multipliers 1/64th of a second apart, the full wave takes one second to generate, corresponding to 60 beats/minute. The computer 20 can readily set the time between multiplier settings so that any reasonable simulated heart rate can be established.

As indicated above, the ambient light simulation circuit 19 serves to drive the LED bar 16 in order to simulate ambient light. Computer 20 controls multiplier M3B of circuit 19 so as to allow for a settable minimum DC current through the LED bar 16.

Figure 2:
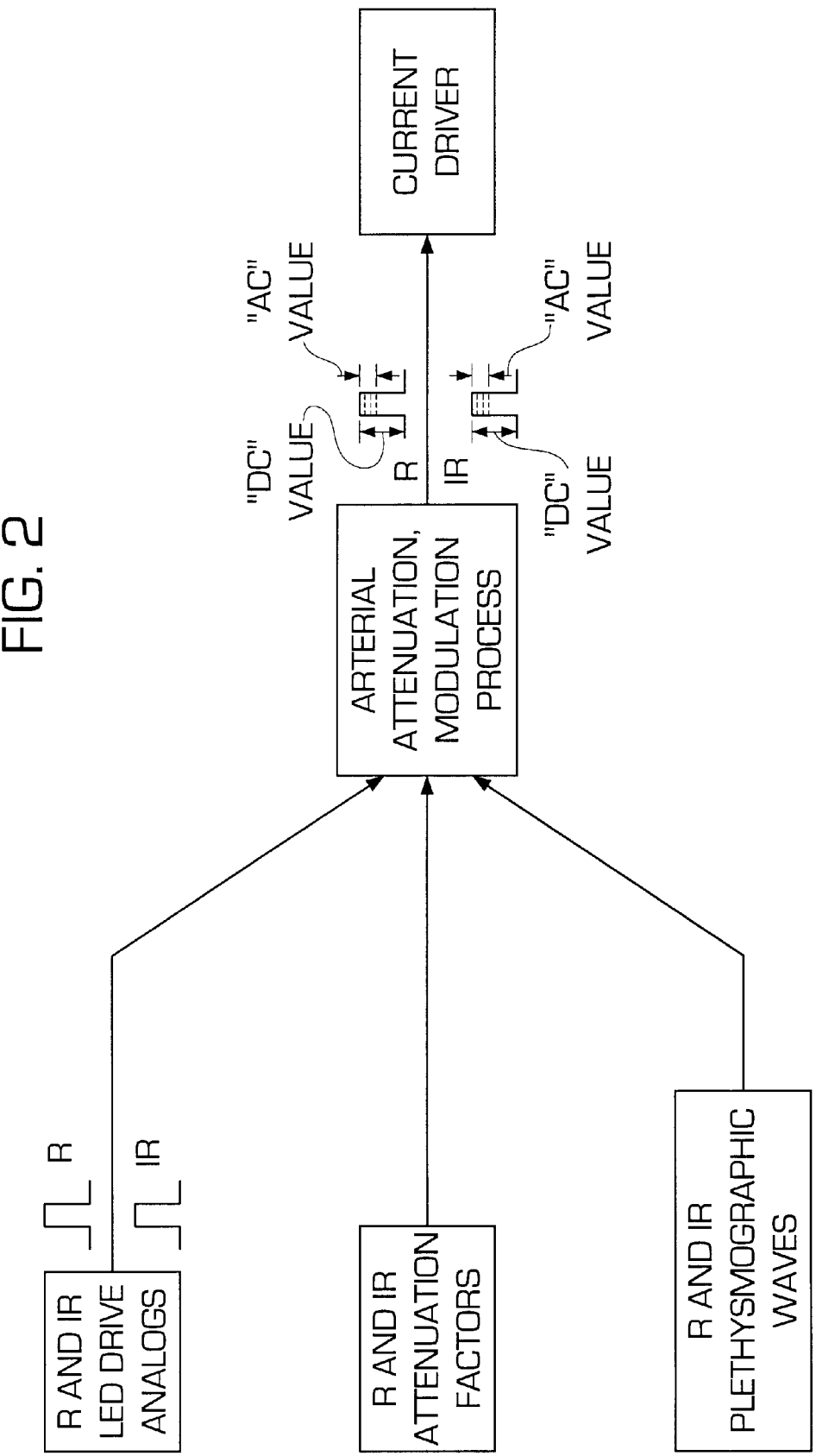
FIG. 2 is a general process model of an attenuation/modulation process of the related art.
Figure 3:
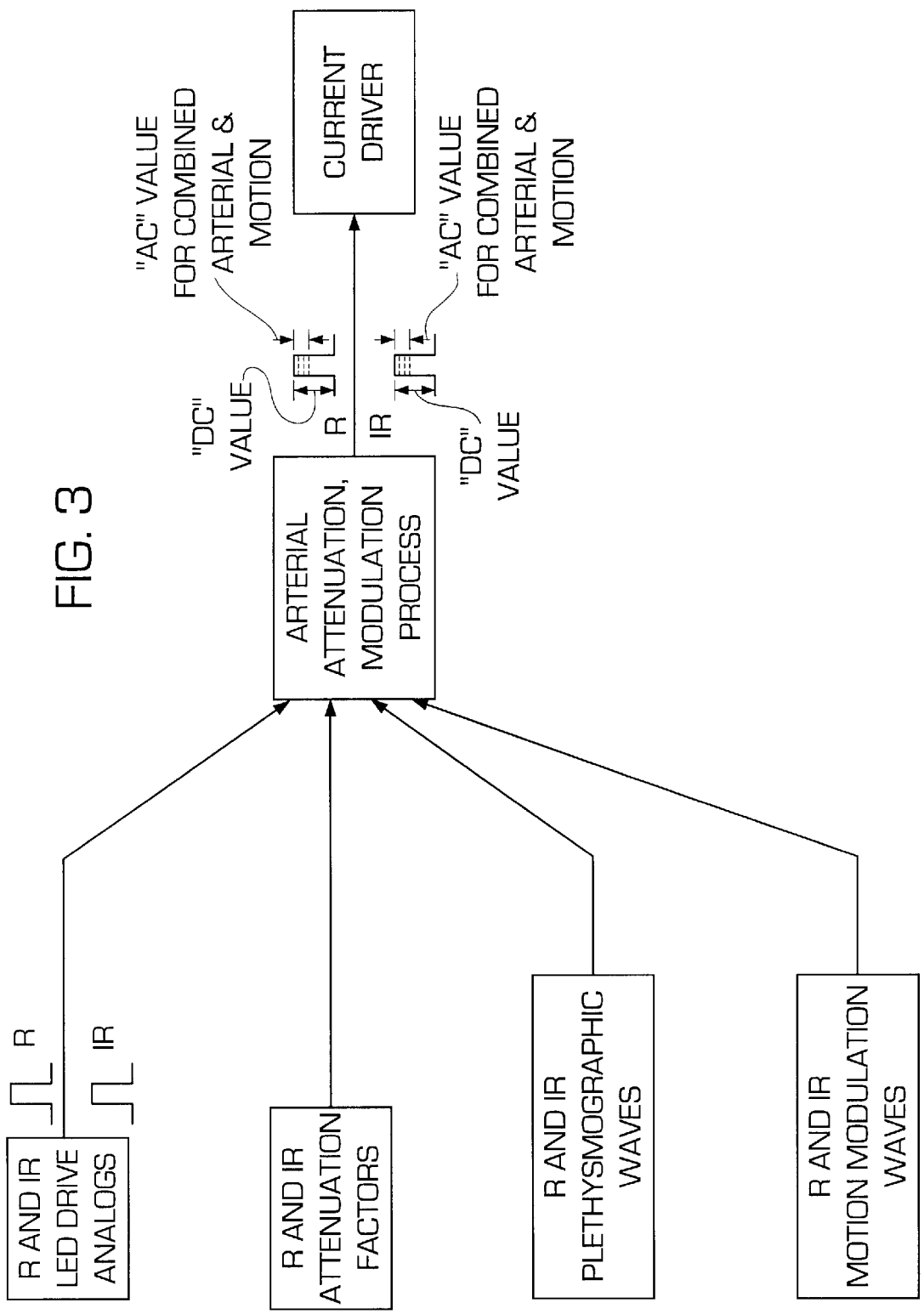
FIG. 3 is a general process model of an attenuation/modulation process, of the present invention, which includes motion simulation.

In an alternative mode of operation, note that switches S1A and S1B can be set in the alternate position to that shown in FIG. 4, thereby providing a DC input to the modulators M1A and M1B. In this mode, the double modulated waves are created as continuous waves and are turned into the required pulse amplitude modulation signal format by Q1. The combined modulating signal is chopped by Q1 to produce the final double modulated result. The above is, therefore, a second example of the many ways the functions of FIG. 2 or 3 may be achieved by those skilled in the related art.

As described above, the new simulation process of the present invention is adaptable to existing hardware in this instance by implementation of appropriate software in computer 20.

The foregoing has shown how motion may be simulated by modulating the red and infra-red pulses of an oximeter with more than one frequency or wave simultaneously.

There are uses for this technology other than for simulating motion simultaneous with arterial oxygenation. One such use is in simulating respiration effects simultaneously with arterial oxygenation. To demonstrate how this technology can simulate respiration, it is necessary to first explain how respiration can be a frequency based parameter that can be detected by an oximeter.

Consider a person taking in a breath. The air being pulled into the lungs is full of oxygen. This oxygen starts to transfer to the blood, and as it does so, the rate of transfer drops. Next, the air in the lungs is expelled, and a new breath taken with a fresh full supply of oxygen. Again, oxygen transfer increases to the rate corresponding to the initial new breath. This process results in a fluctuation of blood oxygen at the frequency of the breath rate; that is, at the respiration rate.

In theory, an oximeter able to detect blood oxygen can extract the oxygen variation due to respiration using appropriate signal processing. In fact, at least one oximeter appears to have achieved this feat. More may be expected to follow. In general the technique takes advantage of the fact that the oximeter sees oxygen variations at both the heartbeat rate and the respiration rate. The heartbeat rate and the respiration rate are different, with the former usually being the higher of the two. This difference in rate makes it possible to use modern signal processing techniques to extract the two frequencies from the oximeter sensor signals. From the above it can be seen that the present invention, which can inject signals of a second frequency wave into the oximeter, in addition to the arterial heartbeat wave, (plethysmographic wave) is ideally adapted to respiration simulation.

Recall that the oxygenation of arterial blood is calculated from the normalized ratio of red fluctuation divided by the normalized ratio of infra-red fluctuation, or:

$$\frac{R_{AC}/R_{DC}}{IR_{AC}/IR_{DC}} = R$$

where R is a value related to blood oxygen, and in the usual oximetry case, to arterial blood oxygen. The values $R_{AC}$ and $R_{DC}$ are the "AC" and "DC" values of the red wave, whereas $IR_{AC}$ and $IR_{DC}$ are the "AC" and "DC" values of the infra-red wave.

It can be seen that if it is desired to introduce a fluctuation into R, the arterial blood oxygen value, then that fluctuation must be introduced into the numerator, the denominator, or both, as may be convenient. If fluctuation is introduced into both, then the fluctuations in the numerator and denominator must be different, or they will cancel out.

It should be recalled that motion makes non-arterial oxygen detectable, at its own R value, separate from arterial oxygen. By contrast, respiration introduces a fluctuation into the arterial oxygen value only.

The technology of the present invention allows manipulation of either the numerator, the denominator, or both.

For example, the present invention can replicate the process used to simulate motion, but suppress the infra-red second frequency modulation signal. This results in a variation of only the numerator in the R equation at that frequency, because only the red second frequency modulation signal is used, which translates to a variation in the oxygen value measured by the oximeter at that frequency. The implementation shown in FIG. 4 allows the oxygen variation thus achieved to be set at a desired frequency below the simulated heart rate, and at an amplitude commensurate with that expected due to respiration.

The implementation shown in FIG. 4 also allows frequencies higher than heart rate to be selected, as is usual in motion simulations. In fact, this particular implementation has a frequency range for a second modulation signal that goes from, for example, 0.333 Hz to 75 Hz. However, with changes common to the art of frequency synthesis, the above range could be readily extended at both ends.

Alternatively, the present invention can replicate the process used to simulate motion, but suppress the red second frequency modulation signal. This results in a variation of only the denominator in the R equation at that frequency, because only the infra-red second frequency modulation signal is used, which translates to a variation in the oxygen value measured by the oximeter at that frequency. The implementation shown in FIG. 4 allows the oxygen variation thus achieved to be set at a desired frequency below the simulated heart rate, and at an amplitude commensurate with that expected due to respiration.

Alternatively, both numerator and denominator of the R equation could be set to a respiration rate, keeping in mind that their amplitude values would have to be different so as not to cancel out.

As mentioned above, the multiple modulations of the red and infra-red oximeter signals may be accomplished either entirely mathematically by computer or by computer controlled hardware in various configurations, or combinations thereof, one such combination being presented herein.

It is possible to simulate arterial oxygen, non-arterial oxygen and respiration simultaneously. The hardware architecture of FIG. 4 can be used for such a simulation. However, at least 2 of the 3 frequency wave values would have to be combined in the computer, as the hardware is designed to support only 2 separate signals for hardware based modulation.

As an aid to understanding of the present invention, think of the red and infra-red oximeter impulses as carriers at two frequencies, much as AM radio waves are carriers at different frequencies, wherein each frequency is capable of carrying voice and music. Because the carrier frequency is much higher than the frequencies of the information impressed on it, it can reproduce them with fidelity. Think of a quartet of musical instruments, or a whole orchestra. A trained listener can extract the melody of each instrument from the radio reproduction, even though they were all mixed on the same carrier.

Similarly, the present invention impresses the waves representative of plethysmographic action, motion and respiration onto the red and infra-red carriers; slightly differently on each depending on the desired effect. The oximeter, then, plays the role of the skilled listener, extracting the appropriate information from each.

There may be other frequency based parameters capable of detection through the oximetry sensing method besides arterial oxygen, non-arterial oxygen, and respiration. If so, it will be apparent to one skilled in the art that the multiple frequency modulation technology of the present invention is able to simulate them.

It is contemplated that numerous modifications may be made to the simulator of the present invention without departing from the spirit and scope of the invention as defined in the following claims.

What is claimed is:

1. A method, for simultaneous simulation of arterial and non-arterial tissue oxygenation which is to be monitored by a pulse oximeter that provides red and infra-red light flashes, comprising:

a) taking as inputs: 1) the oximeter's light flashes; 2) a first waveform representative of fluctuating arterial attenuation of an optical path through tissue; and 3) a second waveform representative of fluctuating non-arterial attenuation of an optical path through tissue, and b) combining said light flashes, said first waveform and said second waveform such that the result is pulses which are amplitude modulated by both said first and second waveforms, whereby said pulse amplitude modulated pulses can be applied to an oximeter for interpretation as attenuations of its light flashes by arterial and non-arterial oxygenated tissue.

2. The method of claim 1, wherein said first waveform includes red and infra-red components and the method further includes varying the percent ratio of the red component to the infra-red component to thereby simulate the arterial attenuation at various blood oxygen levels.

3. The method of claim 1, wherein said second waveform includes red and infra-red components and the method further includes varying the percent ratio of the red component to the infra-red component to thereby simulate the non-arterial attenuation at various blood oxygen levels.

4. A method, for simultaneous simulation of arterial and non-arterial tissue oxygenation which is to be monitored by a pulse oximeter that provides red and infra-red light flashes, comprising:
   a) taking as inputs: 1) an electrical analogue of the oximeter's light flashes; 2) a first waveform representative of fluctuating arterial attenuation of an optical path through tissue; and 3) a second waveform representative of fluctuating non-arterial attenuation of an optical path through tissue, and
   b) combining said electrical analogue, said first waveform and said second waveform such that the result is pulses which are amplitude modulated by both said first and second waveforms, whereby said pulse amplitude modulated pulses can be applied to an oximeter for interpretation as attenuations of its light flashes by arterial and non-arterial oxygenated tissue.

5. The method of claim 4, wherein said first waveform includes red and infra-red components and the method further includes varying the percent ratio of the red component to the infra-red component to thereby simulate the arterial attenuation at various blood oxygen levels.

6. The method of claim 4, wherein said second waveform includes red and infra-red components and the method further includes varying the percent ratio of the red component to the infra-red component to thereby simulate the non-arterial attenuation at various blood oxygen levels.

7. A method for sensing and modulating the red and infra-red signals of a pulse oximeter to simultaneously simulate arterial and non-arterial oxygen, by dual modulation of the red and infra-red signals, comprising:
   sensing red and infra-red signals of the pulse oximeter;
   modulating the signals to provide a simulated arterial oxygen value, blood pressure wave form, blood pressure wave shape, wave frequency, and wave amplitude;
   also modulating the signals to provide a non-arterial oxygen value, motion wave form, wave shape, wave frequency, and wave amplitude, to thereby form double modulated signals; and
   conveying the double modulated signals to an oximeter photo diode input.

8. The method of claim 7, wherein said step of modulating the signals to provide a simulated arterial oxygen value includes varying the percent ratio of red to infra-red signals so as to simulate any desired arterial oxygen value.

9. The method of claim 7, wherein said step of also modulating the signals to provide a non-arterial oxygen value includes varying the percent ratio of red to infra-red signals so as to simulate any desired non-arterial oxygen value.

10. A method for simultaneous simulation of arterial and non-arterial tissue oxygenation which is to be monitored by a pulse oximeter that operates on the principle of differential absorbance of two light frequencies by blood oxygen, comprising:
   a) sensing oximeter signals used for generating the two different light frequencies, and creating electrical analogues thereof;
   b) modulating said electrical analogues to simulate a non-arterial oxygen value, motion wave form, wave shape, wave frequency, and wave amplitude;
   c) additionally modulating said analogues to simulate an arterial oxygen value, blood pressure wave form, blood pressure wave shape, wave frequency, and wave amplitude to form doubly modulated analogous; and
   d) applying the doubly modulated analogues to a current driver to drive a photo diode input of the oximeter, such that both arterial and non-arterial behavior of living tissue is simulated.

11. The method of claim 10, wherein step (b) includes modulating the electrical analogues to simulate various non-arterial oxygen values within a range of from 0 to 100%.

12. The method of claim 10, wherein step (c) includes additionally modulating the analogues to simulate various arterial oxygen values within a range of from 0 to 100%.

13. A method for creating pulse oximetry simulation signals, comprising:
   taking as inputs:
      (a) red and infra-red LED drive pulse analogs of a pulse oximeter;
      (b) red and infra-red attenuation factors which establish the simulated bulk attenuation of tissue;
      (c) red and infra-red arterial modulation waveforms whose ratios and absolute amplitudes determine oxygen value and signal strength, and whose fundamental frequency determines simulated heartbeats/minute; and
      (d) red and infra-red motion modulation waveforms whose ratios and absolute amplitudes determine oxygen value and signal strength of the motion, and whose fundamental frequency determines simulated motion waves/minute;
   combining inputs (a), (b), (c), and (d) so as to form output red and infra-red pulses, which are pulse amplitude modulated versions of the red and infra-red drive pulse analogs, by:
      (1) using the pulse timing of the red and infra-red LED drive pulse analogs as the output red and infra-red pulse timing;
      (2) setting the output red and infra-red pulses unmodulated amplitude level by the red and infra-red attenuation factors, respectively;
      (3) amplitude modulating the output red and infra-red pulses amplitude by the red and infra-red plethysmographic waves, respectively;
      (4) amplitude modulating the output red and infra-red pulses amplitude by the red and infra-red motion waves, respectively;
   in order to impress, upon the original drive pulse analogs, appropriate attenuations and modulations to physiologically simulate both arterial and motion characteristics which can be read by the pulse oximeter in a predetermined way.

14. The method of claim 13, further comprising, before said step of combining, varying the ratio of said red and infra-red arterial modulation waveforms to thereby simulate different oxygen values within a range of from 0 to 100%.

15. The method of claim 13, further comprising, before said step of combining, varying the ratio of said red and infra-red motion modulation waveforms to thereby simulate different non-arterial oxygen values within a range of from 0 to 100%.

16. The method of claim 13, wherein the step of taking (d) as an input includes taking red motion modulation waveforms which are continuous waves, and infra-red motion modulation waveforms which are continuous, to simulate shivering.

17. The method of claim 13, wherein the step of taking (d) as an input includes taking a single red motion modulation waveform, and a single infra-red motion modulation waveform, to simulate a bumped probe event.

18. An apparatus for simultaneous simulation of arterial and non-arterial tissue oxygenation which is to be monitored by a pulse oximeter that provides red and infra-red light flashes, the apparatus comprising:

first means for converting the red and infra-red light flashes of the pulse oximeter into electrical signals;

means for generating a first waveform representative of fluctuating arterial attenuation of an optical path through tissue;

means for generating a second waveform representative of fluctuating non-arterial attenuation of an optical path through tissue;

means for combining said electrical signals with said first and second waveforms so as to form pulses which are amplitude modulated by both said first and second waveforms; and means for converting said pulses to converted light flashes and for transmitting the converted light flashes to the pulse oximeter for detection so that the pulse oximeter responds to the converted light flashes as it would to light flashes modulated by living tissue.

19. The apparatus of claim 18, wherein said first waveform includes red and infra-red components, and said means for generating a first waveform includes means for varying the ratio of the red component to the infra-red component to thereby simulate the arterial attenuation at various blood oxygen levels.

20. The apparatus of claim 18, wherein said second waveform includes red and infra-red components, and said means for generating a second waveform includes means for varying the ratio of the red component to the infra-red component to thereby simulate the non-arterial attenuation at various blood oxygen levels.

21. An apparatus for simultaneous simulation of arterial and non-arterial tissue oxygenation which is to be monitored by a pulse oximeter that provides red and infra-red light flashes, the apparatus comprising:

first means for receiving electrical signals from the pulse oximeter;

means for generating a first waveform representative of fluctuating arterial attenuation of an optical path through tissue;

means for generating a second waveform representative of fluctuating non-arterial attenuation of an optical path through tissue;

means for combining said electrical signals with said first and second waveforms so as to form pulses which are amplitude modulated by both said first and second waveforms; and means for transmitting the pulses to the pulse oximeter for detection.

22. The apparatus of claim 21, wherein said first waveform includes red and infra-red components, and said means for generating a first waveform includes means for varying the ratio of the red component to the infra-red component to thereby simulate the arterial attenuation at various blood oxygen levels.

23. The apparatus of claim 21, wherein said second waveform includes red and infra-red components, and said means for generating a second waveform includes means for varying the ratio of the red component to the infra-red component to thereby simulate the non-arterial attenuation at various blood oxygen levels.

24. An apparatus for simultaneous simulation of arterial and non-arterial tissue oxygenation which is to be monitored by a pulse oximeter that provides red and infra-red LED drive signals, the apparatus comprising:

a first circuit which converts the red and infra-red LED drive signals of the pulse oximeter into analogous electrical signals;

circuit elements which generate first waveforms representative of fluctuating red and infra-red arterial attenuation of an optical path through tissue;

other circuit elements which generate second waveforms representative of fluctuating red and infra-red non-arterial attenuation of an optical path through tissue;

a summation amplifier connected to said circuit elements and to said other circuit elements so as to combine said electrical signals with said waveforms so as to form pulses which are amplitude modulated by both said first waveform and said second waveform; and a second circuit, connected to said summation amplifier, which transmits said combined signals to the pulse oximeter for detection so that the pulse oximeter responds to the converted light flashes as it would to light flashes modulated by living tissue.

25. An apparatus for simultaneous simulation of arterial and non-arterial tissue oxygenation which is to be monitored by a pulse oximeter that provides electrical signals, the apparatus comprising:

an input configured to receive the electrical signals from the pulse oximeter;

a pair of first circuit elements which generate a first waveform representative of fluctuating arterial attenuation of an optical path through tissue;

a pair of second circuit elements which generate a second waveform representative of fluctuating non-arterial attenuation of an optical path through tissue;

a summation circuit element connected to said pair of first circuit elements, to said pair of second circuit elements, and to said input so as to combine said electrical signals with said first and second waveforms so as to form pulses which are amplitude modulated by both said first and second waveforms; and a circuit, connected to said summation circuit element, which transmits the pulses to the pulse oximeter for detection.

26. A stimulator comprising an arrangement of modulators which, when applied to the electrical analogues of an oximeter's red and infra-red LED drive signals, permits simulation of bulk tissue attenuation, tissue motion induced modulation and tissue heartbeat induced modulation, so that the resulting attenuated and modulated analogues, when conveyed to an oximeter's photo diode input, are interpreted in a predetermined manner so as to convey motion and arterial blood oxygen values.

27. The stimulator of claim 26, wherein the modulators are arranged so that any one of various arterial blood oxygen values is conveyed.

28. A method for simultaneous simulation of arterial and respiratory tissue oxygenation, comprising:

a) sensing red and infra-red signals of a pulse oximeter;

b) modulating the red and infra-red signals to provide a simulated arterial oxygen value;

c) amplitude modulating, at a respiration frequency, at least one of the red and infra-red signals to provide a respiratory tissue oxygenation value, so that said at least one of the red and infra-red signals is double modulated; and d) conveying the modulated red and infra-red signals to an oximeter photo diode input.

29. The method of claim 28, wherein step (b) includes modulating the red and infra-red signals so as to provide different simulated arterial oxygen values.

30. The method of claim 28, wherein step (c) consists of amplitude modulating, at a respiration frequency, only said red signal.

31. The method of claim 28, wherein step (c) consists of amplitude modulating, at a respiration frequency, only said infra-red signal.

32. The method of claim 28, wherein step (c) includes amplitude modulating, at a respiration frequency, both said red and infra-red signals by different amounts.

33. The method of claim 28, further comprising, between step (c) and step (d):

(e) modulating said red and infra-red signals to provide a simulated non-arterial oxygen value, so that step (d) includes conveying at least one triple modulated signal to the oximeter photo diode input.

34. The method of claim 33 wherein step (e) includes modulating the red and infra-red signals so as to provide different simulated non-arterial oxygen values.

35. The method of claim 33, wherein step (c) consists of amplitude modulating, at a respiration frequency, only said red signal.

36. The method of claim 33, wherein step (c) consists of amplitude modulating, at a respiration frequency, only said infra-red signal.

37. The method of claim 33, wherein step (c) includes amplitude modulating, at a respiration frequency, both said red and infra-red signals by different amounts.

38. A method for simultaneous simulation of arterial tissue oxygenation and other parameters, comprising:

a) sensing red and infra-red signals of a pulse oximeter;

b) modulating the red and infra-red signals to provide a simulated arterial oxygen value;

c) amplitude modulating, at a predetermined frequency, at least one of the red and infra-red signals to simulate a parameter, so that said at least one of the red and infra-red signals is double modulated;

d) repeating step (c) with a different modulation to simulate an additional parameter;

e) repeating step (d) to simulate additional parameters, as necessary; and f) conveying the modulated red and infra-red signals to an oximeter photo diode input.

39. The method of claim 38, wherein step (b) includes modulating the red and infra-red signals so as to provide different simulated arterial oxygen values.

40. The method of claim 38, wherein step (c) comprises amplitude modulating, at a respiration frequency, at least one of the red and infra-red signals to provide a respiratory tissue oxygenation value.

41. The method of claim 40, wherein step (c) consists of amplitude modulating, at a respiration frequency, only said red signal.

42. The method of claim 40, wherein step (c) consists of amplitude modulating, at a respiration frequency, only said infra-red signal.

43. The method of claim 40, wherein step (c) includes amplitude modulating, at a respiration frequency, both said red and infra-red signals by different amounts.

* * * * *